United States Patent [19]

Stafford et al.

[11] Patent Number: 5,297,303

[45] Date of Patent: Mar. 29, 1994

[54] EXAMINATION TABLE TOP

[76] Inventors: Teresa E. Stafford, R.R. #1, Box 77, Attica, Ind. 47918-9729; Karen E. Davis, 805 S. Brady St., Attica, Ind. 47918

[21] Appl. No.: 51,773

[22] Filed: Apr. 26, 1993

[51] Int. Cl.$^5$ .......................... A61G 7/10; A61G 13/00
[52] U.S. Cl. .............................................. 5/613; 5/621; 5/632
[58] Field of Search ................... 5/613, 621, 600, 601, 5/900.5; 378/209; 606/242

[56] References Cited

U.S. PATENT DOCUMENTS

| 4,596,384 | 6/1986 | Blosser | 5/613 |
| 4,648,389 | 3/1987 | Kowalski et al. | 5/613 |
| 5,095,569 | 3/1992 | Glenn | 5/632 |

Primary Examiner—Alexander Grosz
Attorney, Agent, or Firm—Leon Gilden

[57] ABSTRACT

A table top is arranged to include a mammary plate, having opposed first and second arcuate recesses to each individually accommodate a mammary during an examination procedure. A modification of the invention includes the mammary plate formed of expandable and contractible relative L-shaped components to accommodate variation in sizing of the first and second arcuate recesses.

4 Claims, 4 Drawing Sheets

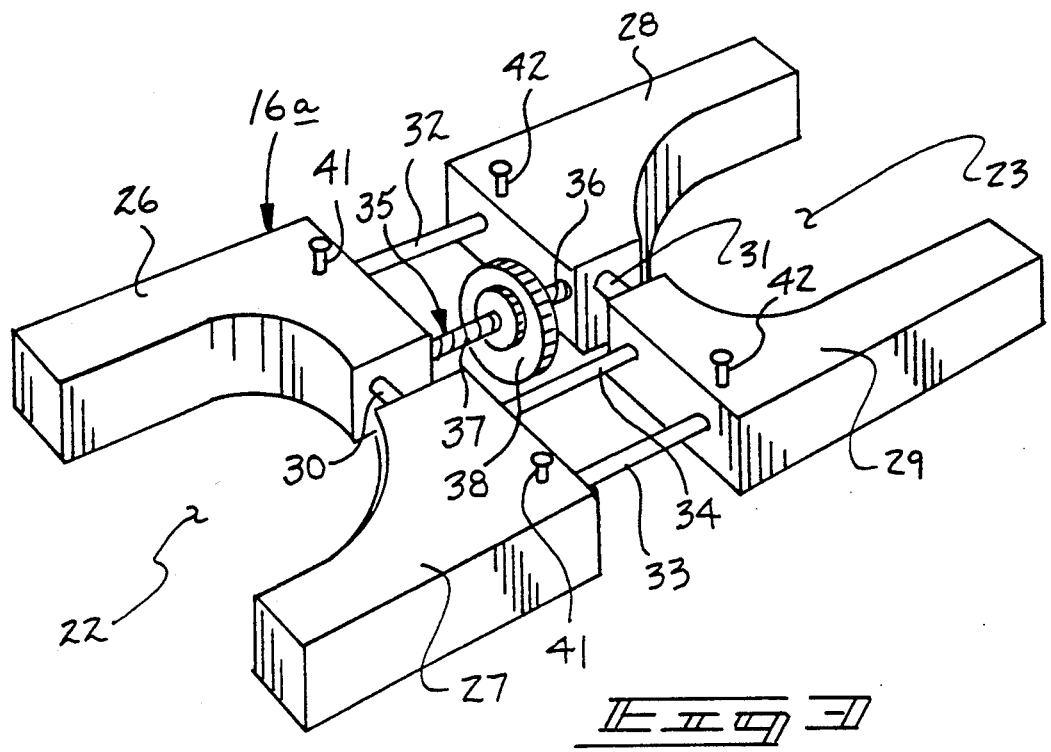
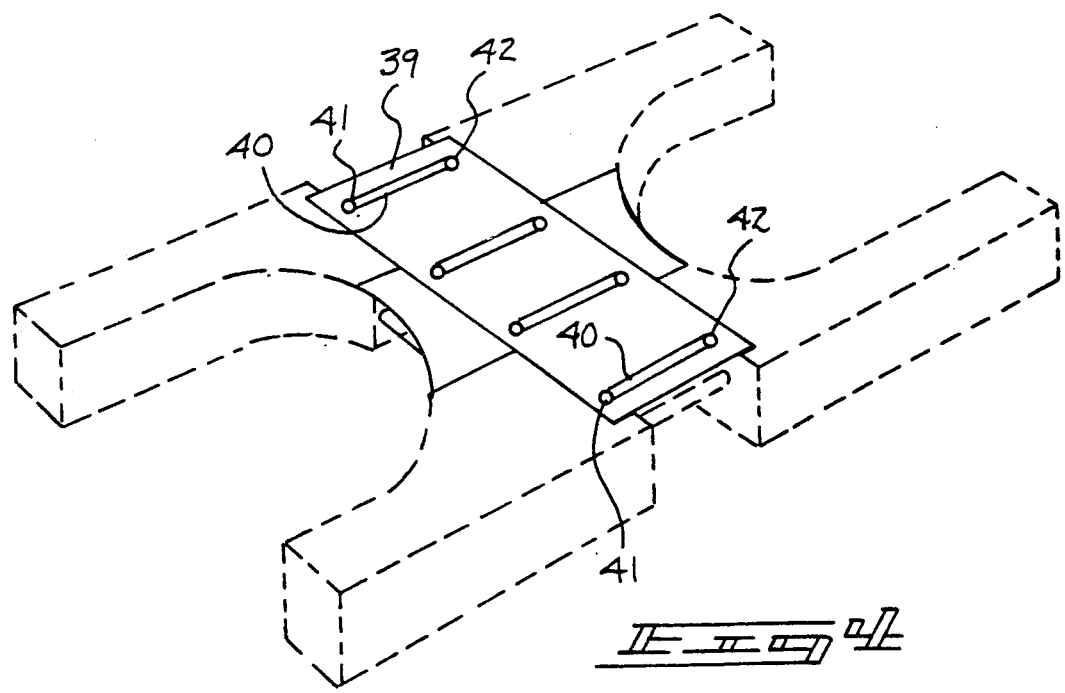

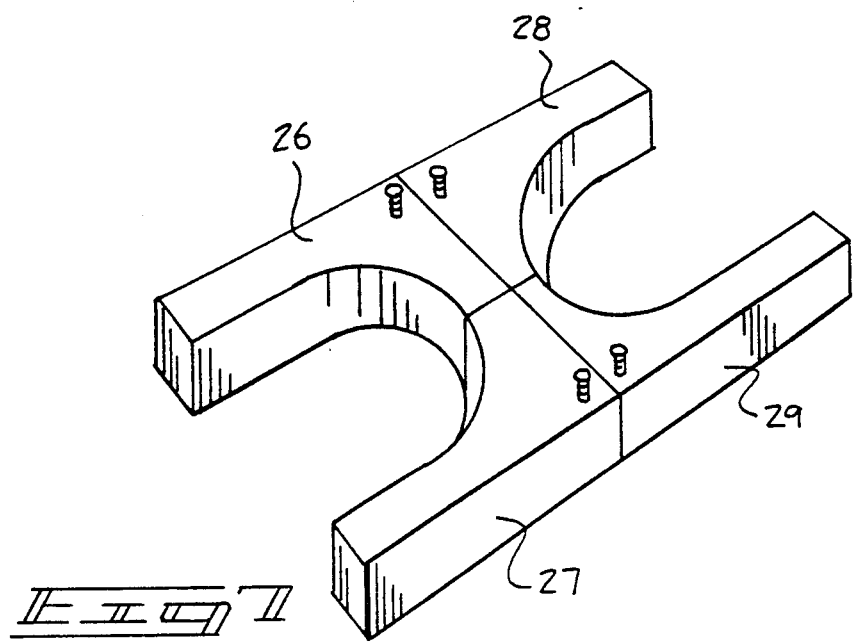
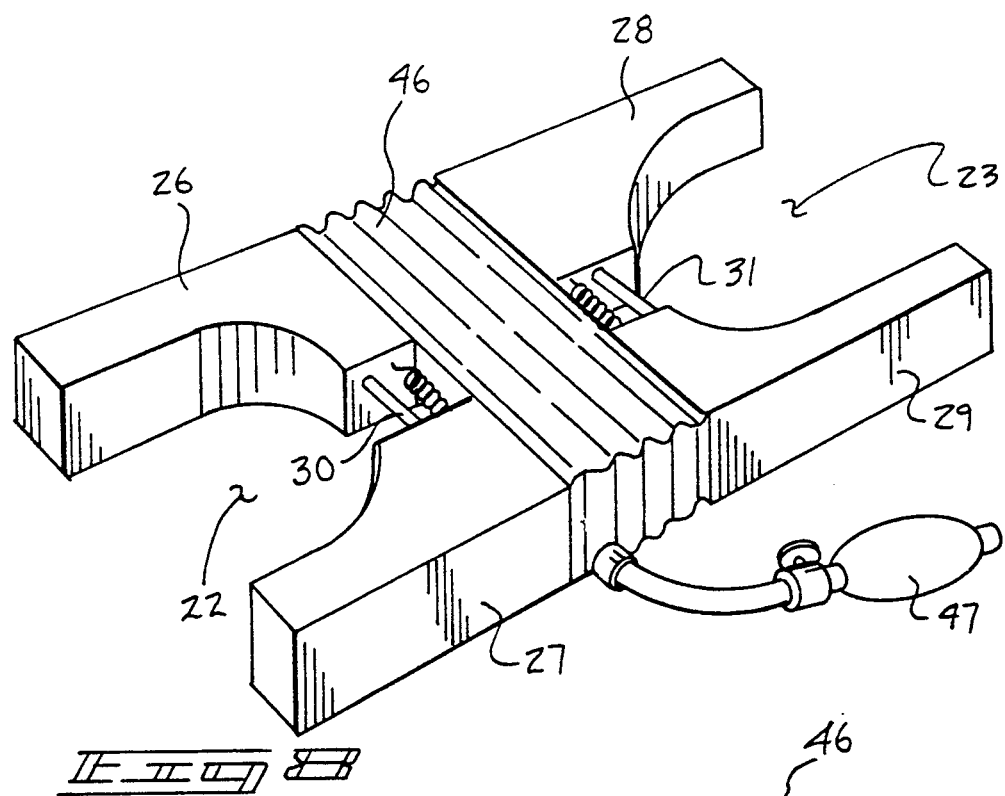
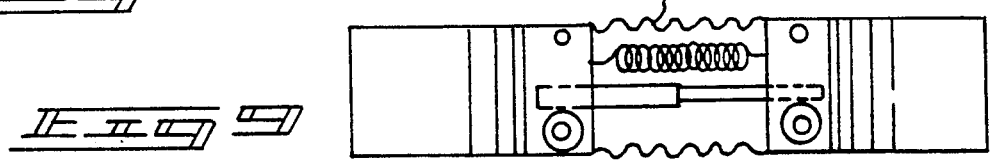

EXAMINATION TABLE TOP

BACKGROUND OF THE INVENTION

1. Field of the Invention

The field of invention relates to examination table structure, and more particularly pertains to a new and improved examination table top arranged to include a mammary plate arranged for orientation within the table top structure.

2. Description of the Prior Art

Various examination tables for use in the medical field have been employed in the prior art wherein theretofore, particularly during breast examination, a table directed to the convenience of positioning the breast portions of a woman in an orientation to permit examination and associated X-ray photography with the organs in a non-compressed state is availed in the instant invention to overcome deficiencies in the prior art in that regard. Examples of prior art examination tables are indicated in U.S. Pat. Nos. 4,982,416; 5,014,292; 5,020,089; and 5,058,871.

SUMMARY OF THE INVENTION

In view of the foregoing disadvantages inherent in the known types of examination table structure now present in the prior art, the present invention provides an examination table top wherein the same is arranged to provide for the efficient orientation of a woman to permit ease of breast examination with the breasts in a non-compressed configuration. As such, the general purpose of the present invention, which will be described subsequently in greater detail, is to provide a new and improved examination table top which has all the advantages of the prior art examination table apparatus and none of the disadvantages.

To attain this, the present invention provides a table top arranged to include a mammary plate, having opposed first and second arcute recesses to each individually accommodate a mammary during an examination procedure. A modification of the invention includes the mammary plate formed of expandable and contractible relative L-shaped components to accommodate variation in sizing of the first and second arcuate recesses.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved examination table top which has all the advantages of the prior art examination table apparatus and none of the disadvantages.

It is another object of the present invention to provide a new and improved examination table top which may be easily and efficiently manufactured and marketed.

It is a further object of the present invention to provide a new and improved examination table top which is of a durable and reliable construction.

An even further object of the present invention is to provide a new and improved examination table top which is susceptible of a low cost of manufacture with regard to both materials and labor, and which accordingly is then susceptible of low prices of safe to the consuming public, thereby making such examination table tops economically available to the buying public.

Still yet another object of the present invention is to provide a new and improved examination table top which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an isometric illustration of a modified mammary plate structure.

FIG. 4 is an indication of a mammary structure including a cover plate.

FIG. 7 is an isometric illustration of the L-shaped portions in a compressed configuration relative to one another.

FIG. 8 is an isometric illustration of the invention including a pneumatic chamber indicated between opposed first and second arcuate recesses.

FIG. 9 is an orthographic cross-sectional illustration of the pneumatic chambers indicated for use by the structure of FIG. 8.

DESCRIPTION OF THE PREFERRED EMBODIMENT

Figure 1:
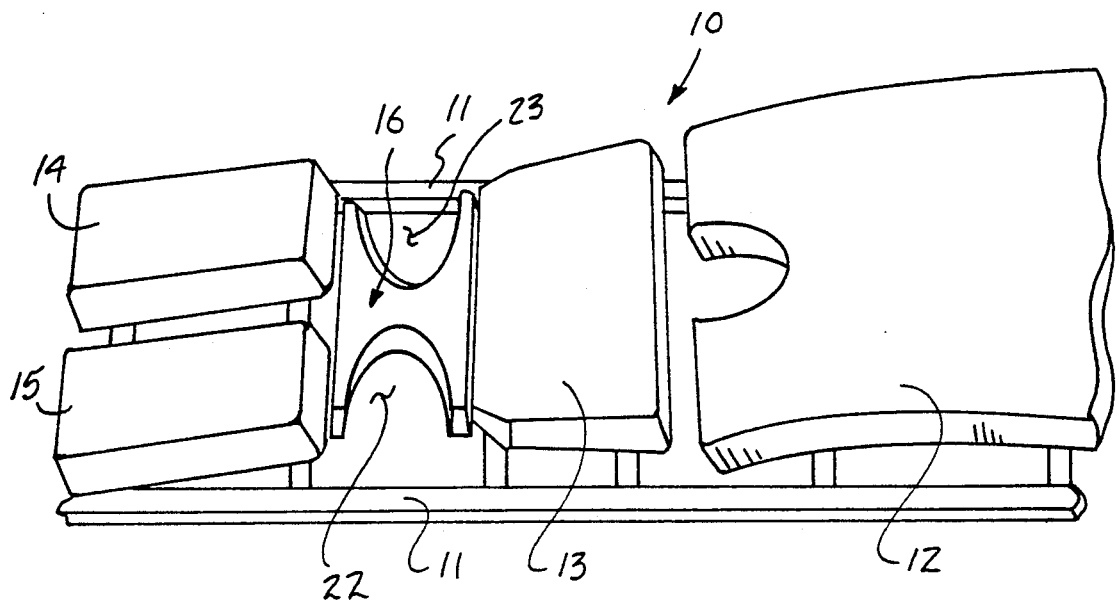
FIG. 1 is an isometric illustration of the table top structure of the invention.
Figure 2:
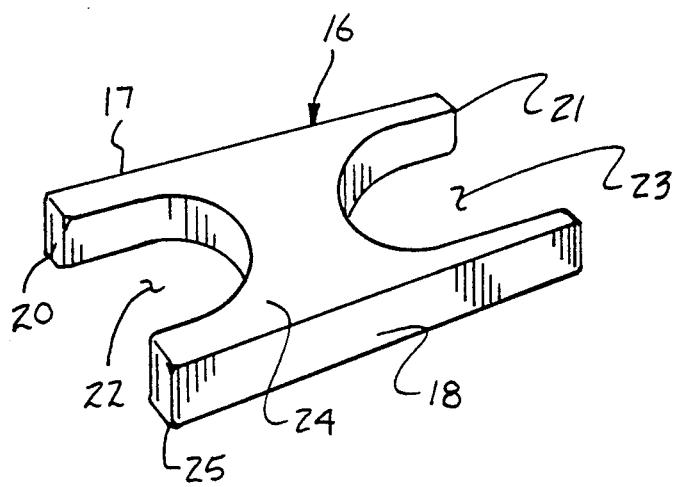
FIG. 2 is an isometric illustration of the mammary plate as employed by the invention.

With reference now to the drawings, and in particular to FIGS. 1 to 9 thereof, a new and improved examination table top embodying the principles and concepts of the present invention and generally designated by the reference numeral 10 will be described.

More specifically, the examination table top 10 of the instant invention is essentially arranged for mounting relative to an X-ray structure, of a type as indicated in U.S. Pat. No. 5,014,292, as well as the U.S. Pat. No. 5,048,071. The table top structure, as indicated in FIG. 1, is arranged to include spaced table rails 11 mounting a first torso cushion 12 in adjacency to a second torso cushion 13, with first and second shoulder cushions 14 and 15 spaced from the second torso cushion 13, having a mammary plate 16 oriented between the first and second shoulder cushions 14 and 15 and the second torso cushion 13, with a mammary plate 16 having a first side wall 17 in adjacency to the first and second shoulder cushions 14 and 15 oriented substantially at an oblique angle thereto and typically at an orthogonal relationship. A second side wall 18 is positioned in adjacency relative to the second torso cushion 13. First and second end walls 20 and 21 respectfully are mounted on opposed sides of the mammary plate 16, with first and second arcuate recesses 22 and 23 directed into the mammary plate from the respective first and second end walls 20 and 21, with the first and second arcuate recesses 22 and 23 directed from the top wall 24 through the bottom wall 25 of the mammary plate.

The modified mammary plate 16a, as indicated in FIG. 3, includes respective first and second L-shaped portions 26 and 27 defining the first arcuate recess 22 therebetween permitting adjustment of the first arcuate recess 22, and wherein third and fourth respective L-shaped portions 28 and 29 define the second arcuate recess 23 therebetween. A first slide rod 30 slidably mounts the first and second L-shaped portions 26 and 27, with a second slide rod 31 parallel to the first slide rod 30 arranged to slidably receive the third and fourth L-shaped portions 28 and 29 therebetween. A third slide rod 32 and a first control rod 35 orthogonally oriented relative to the first and second slide rods 30 and 31 extend between the first and third L-shaped portions 26 and 28, with the first control rod 35 having respective right and left hand threaded portions 36 and 37 threadedly directed into the respective third and first L-shaped portions 28 and 26, whereupon a spin wheel 38 fixedly mounted at an interface between the right and left hand threaded portions 36 and 37 permits ease of rotation of the control rod 35 to effect projection towards and away relative to one another of the first and third L-shaped portions 26 and 28. It should be noted that upon projection and displacement of the first and third L-shaped portions 26 and 28 relative to one another, the second and fourth L-shaped portions associated with respective first and third L-shaped portions move simultaneously and concurrently therewith. Fourth and fifth slide rods 33 and 34 are oriented parallel to the third slide rod 32 and the first control rod 35 and mounted slidably between the second and fourth L-shaped portions 27 and 29.

The FIG. 4 indicates the use of a cover plate 39 having parallel slots 40, with the parallel slots 40 oriented parallel between the third, fourth, and fifth slide rods 32, 33, and 34, wherein first guide pins 41 mounted to the first and second L-shaped portions 26 and 27 and second guide pins 42 mounted to the third and fourth L-shaped portions 28 and 29 are received within opposed ends of the slots 40. The cover plate 39 in this manner accommodates displacement of the pairs of L-shaped portions towards and away from one another in providing a cover plate to bridge the gapping and spacing of the L-shaped portions relative to one another.

Figure 5:
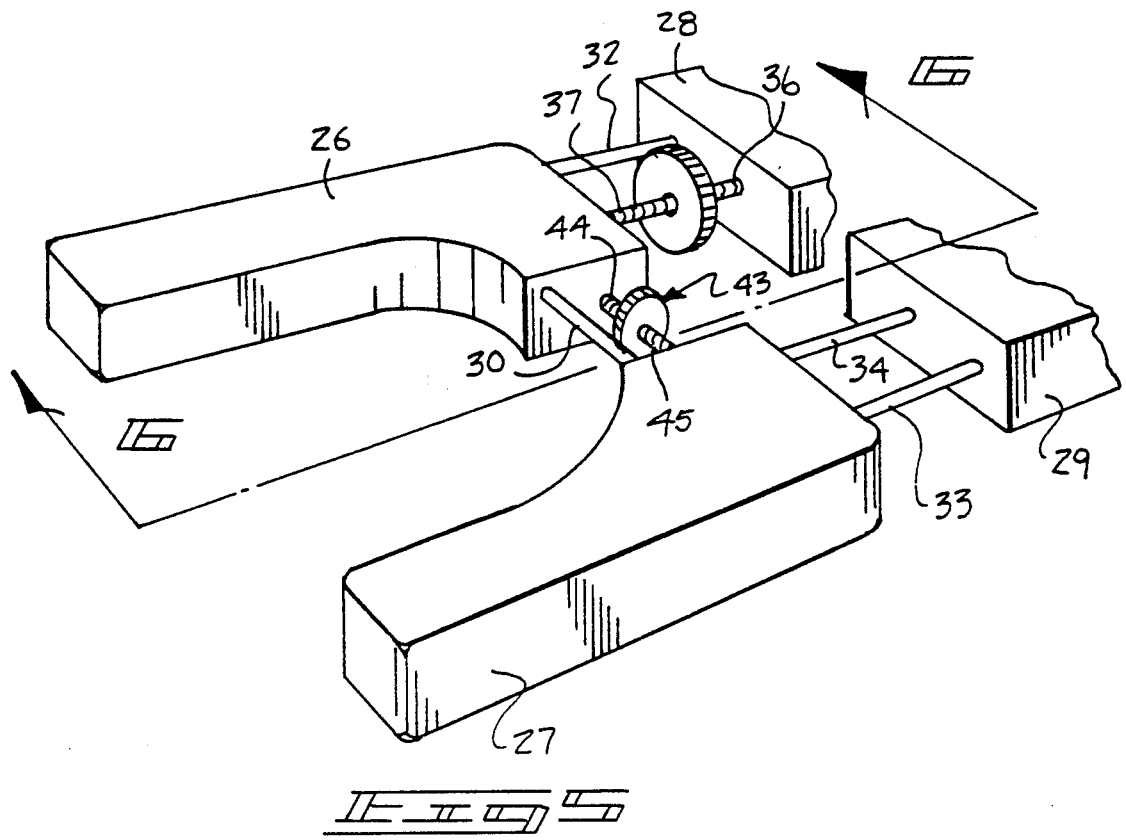
FIG. 5 is an enlarged isometric illustration of the invention to further include a second control rod between adjacent L-shaped portions.
Figure 6:
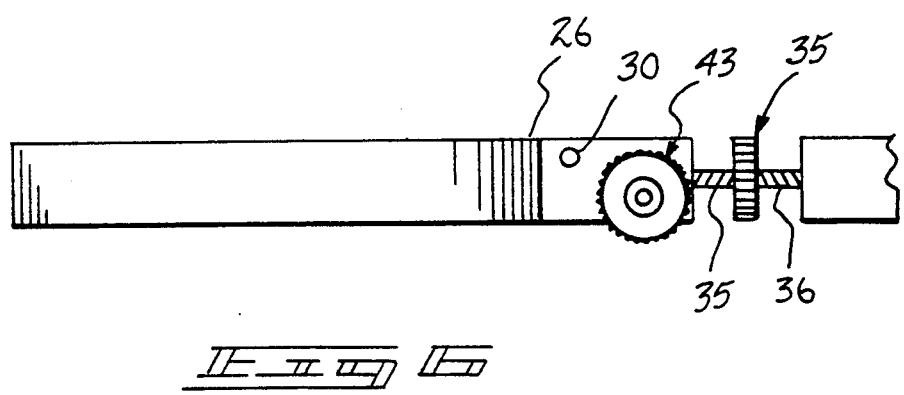
FIG. 6 is an orthographic view, taken along the lines 6—6 of FIG. 5 in the direction indicated by the arrows.

The FIG. 5 indicates the use of a second control rod 43 directed between the first and second L-shaped portions 26 and 27 in addition to the first slide rod 30, with the second control rod 43 parallel to the first slide rod 30. The second control rod 43 includes respective second right and left hand portions 45 and 44 received within the respective received within the respective second and first L-shaped portions 26 and 27 to effect the control displacement of the first and second L-shaped portions 26 and 27 relative to one another to thereby effect simultaneous displacement of the third and fourth L-shaped portions 28 and 29 relative to one another.

The FIGS. 8 and 9 indicate the use of a pneumatic chamber 46 operative by pneumatic pump for inflation mounted between the first pair of L-shaped portions 26 and 27 relative to the second pair of L-shaped portions 28 and 29 to effect displacement of the L-shaped portions relative to one another, wherein a retraction spring mounted within the pneumatic chamber 46 is arranged to direct the pairs of L-shaped portions towards one another, as indicated.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. An examination table top including at least one torso cushion, the at least one torso cushion spaced from a first shoulder cushion and a second shoulder cushion, with the second cushion and the first shoulder cushion arranged in adjacency and in a coextensive relationship relative to one another, and a mammary plate positioned between the first shoulder cushion, the second shoulder cushion, and the torso cushion, the mammary plate including a first side wall spaced from a second side wall, a first end wall spaced from a second end wall, a top wall spaced from a bottom wall, with the first side wall positioned in adjacency to the first shoulder cushion and the second shoulder cushion oriented at an oblique angulation relative to the first shoulder cushion and the second shoulder cushion, and the second side wall positioned in adjacency relative to said torso cushion, and the first end wall including a first arcuate recess directed into the mammary plate from the first end wall, and a second arcuate recess of a mirror image configuration relative to said first arcuate recess directed into the mammary plate from said second end wall, with the first arcuate recess and the second arcuate recess arranged in a spaced orientation relative to one another longitudinally aligned relative to one another.

2. A table top as set forth in claim 1 wherein the mammary plate includes a first L-shaped portion arranged in a coextensive mirror image relationship relative to a second L-shaped portion, having said first arcuate recess oriented between said first L-shaped portion and said second L-shaped portion, and a third L-shaped portion arranged in a coextensive mirror image relationship relative to a fourth L-shaped portion, wherein the third L-shaped portion and the fourth L-shaped portion define said second arcuate recesses therebetween, and a first slide rod slidably mounted within said first L-shaped portion and said second L-shaped portion in adjacency to said first arcuate recess, and a second slide rod slidably directed into said third L-shaped portion and said fourth L-shaped portion in adjacency to said second arcuate recess, wherein the first slide rod and the second slide rod are arranged in a parallel relationship relative to one another, and a third slide rod orthogonally oriented relative to said first slide rod and said second slide rod, with the third slide rod slidably mounted between said first L-shaped portion and said third L-shaped portion, and a fourth slide rod slidably directed into said second L-shaped portion and said fourth L-shaped portion, with the third slide rod and the fourth slide rod arranged in a parallel relationship relative to one another, and a control rod threadedly directed into said first L-shaped portion and into said third L-shaped portion, with the control rod having a right hand thread threadedly received within said third L-shaped portion and a left hand threaded portion received within said first L-shaped portion, wherein rotation of said control rod effects longitudinal displacement of said first L-shaped portion relative to said third L-shaped portion.

3. A table top as set forth in claim 2 wherein the first L-shaped portion and the second L-shaped portion each include a first guide pin, and the third L-shaped portion and the fourth L-shaped portion each include a second guide pin, and a cover plate, the cover plate including a plurality of parallel slots, wherein one of said slots includes and slidably receives one of said first guide pins and one of said second guide pins, and a further of said L-shaped slots receives a further one of said first guide pins and said second guide pins, with the cover plate extending over said third slide rod, said fourth slide rod, and said control rod.

4. A table top as set forth in claim 3 including a second control rod, having a second left hand portion threadedly received within said first L-shaped portion, and a second right hand threaded portion received within said second L-shaped portion, whereupon rotation of said second control rod effects selective displacement of said first L-shaped portion and said second L-shaped portion relative to one another and simultaneous displacement of said third L-shaped portion relative to said fourth L-shaped portion relative to one another.

* * * * *